United States Patent
Brannon

(10) Patent No.: US 10,078,063 B2
(45) Date of Patent: Sep. 18, 2018

(54) THERMOGRAPHIC ANALYSIS OF POLYMERIC MATERIALS

(71) Applicant: COLORMATRIX HOLDINGS, INC., Wilmington, DE (US)

(72) Inventor: Phillip Brannon, Knowsley Merseyside (GB)

(73) Assignee: COLORMATRIX HOLDINGS, INC., Wilmington, DE (US)

( * ) Notice: Subject to any disclaimer, the term of this patent is extended or adjusted under 35 U.S.C. 154(b) by 77 days.

(21) Appl. No.: 15/504,664

(22) PCT Filed: Aug. 10, 2015

(86) PCT No.: PCT/GB2015/052307
§ 371 (c)(1),
(2) Date: Feb. 17, 2017

(87) PCT Pub. No.: WO2016/027064
PCT Pub. Date: Feb. 25, 2016

(65) Prior Publication Data
US 2017/0261451 A1 Sep. 14, 2017

(30) Foreign Application Priority Data

Aug. 19, 2014 (GB) .................................. 1414666.6

(51) Int. Cl.
*G01N 25/72* (2006.01)
*G01N 33/44* (2006.01)
(Continued)

(52) U.S. Cl.
CPC ............ *G01N 25/72* (2013.01); *G01J 5/0255* (2013.01); *G01J 5/0875* (2013.01); *G01J 5/10* (2013.01);
(Continued)

(58) Field of Classification Search
None
See application file for complete search history.

(56) References Cited

U.S. PATENT DOCUMENTS

| 4,410,381 A | 10/1983 | Chapman, II |
| 4,956,538 A | 9/1990 | Moslehi |

(Continued)

FOREIGN PATENT DOCUMENTS

| CN | 203484357 U | 3/2014 |
| EP | 1 342 550 A1 | 9/2003 |

(Continued)

*Primary Examiner* — Edwin Gunberg
(74) *Attorney, Agent, or Firm* — Fay Sharpe LLP

(57) ABSTRACT

Apparatus (2) includes a platform (14) on which is supported, via spaced apart posts (16), a stationary rigid support disc (17). Between the platform (14) and disc (17), plaque holder (18) is rotatably mounted. The plaque holder is arranged to hold a plaque (19) for assessment. The plaque is made by injection molding from a composition comprising a polymeric material and a specific amount of reheat additive(s) and any other additives(s) to be assessed. The plaque holder is arranged to move the plaque relative to the disc (17). In an input position, the plaque holder (18) is arranged directly underneath opening (20). In a measurement position, which is 90° from the input position, there are provided first and second temperature measuring assemblies (24, 26) arranged to measure the temperature of the top and bottom surfaces of a plaque held in the plaque holder. The plaque holder can be rotated through 90° from the measurement position to a heating position, wherein the plaque is positioned directly below a heat lamp. In use, the plaque holder is rotated to the heating position, wherein the plaque is heated by the lamp for a predetermined time. Then the plaque holder is rapidly rotated back to the measurement position, wherein the temperatures of the upper and lower surfaces of the plaque are rapidly measured. These steps are (Continued)

repeated and data recorded to allow reheat and/or other characteristics of the plaque to be assessed over time.

20 Claims, 14 Drawing Sheets

(51) Int. Cl.
*G01J 5/10* (2006.01)
*G01J 5/08* (2006.01)
*G01J 5/02* (2006.01)
G01J 5/00 (2006.01)

(52) U.S. Cl.
CPC ...... *G01N 33/44* (2013.01); *G01J 2005/0081* (2013.01)

(56) References Cited

U.S. PATENT DOCUMENTS

| | | |
|---|---|---|
| 2008/0224044 A1 | 9/2008 | SempriMoschnig et al. |
| 2011/0236518 A1 | 9/2011 | Cetinel et al. |
| 2013/0026365 A1 | 1/2013 | Jahnke et al. |
| 2014/0166642 A1 | 6/2014 | Kursawe et al. |

FOREIGN PATENT DOCUMENTS

| | | |
|---|---|---|
| WO | 03/069324 A1 | 8/2003 |
| WO | 2005/108978 A1 | 11/2005 |
| WO | 2009/109777 A1 | 9/2009 |

| TEST REPORT | |
|---|---|
| TEST NAME | GLACIER WHITE WITH SMARTHEAT ACTIVE RATE OF 4PPM |

| Test Time & Date | ✱ |
|---|---|
| Polymer ID | C93 |
| Additive ID | Glacier White |
| Additive Reference | CN120815001-CN131213014-CN13073000-3-581-20028-3 – TIN |
| Additive Rate | 1 % |
| Additive Concentration | 60 % |
| Lamp Power | 65 % |
| Number of Samples | 10 |

| Top Temp Required | 0.00 °C | | Bottom Temp Required | 0.00 °C |
|---|---|---|---|---|
| Individual Heat Exposure Time | 3100 mSec | | | |
| Starting Air Temp | 23.63 °C | | Ending Air Temp | 23.61 °C |
| Starting Steelwork Temp | 23.66 °C | | Ending Steelwork Temp | 23.66 °C |

| HEATING STEPS/SAMPLES ||| | CONDITIONING STEPS/SAMPLES ||||
|---|---|---|---|---|---|---|---|
| Sample Time | Top Temp | Bottom Temp | | Sample Time | | Top Temp | Bottom Temp |
| 100 mSec | 22.10 °C | 21.63 °C | 1 | 32800 mSec | | 143.42 °C | 69.02 °C |
| 3700 mSec | 59.72 °C | 24.51 °C | 2 | 33200 mSec | | 141.31 °C | 70.73 °C |
| 7300 mSec | 79.14 °C | 28.34 °C | 3 | 34200 mSec | | 137.39 °C | 71.50 °C |
| 10900 mSec | 91.73 °C | 33.85 °C | 4 | 35200 mSec | | 133.59 °C | 73.41 °C |
| 14500 mSec | 103.32 °C | 38.65 °C | 5 | 36200 mSec | | 130.82 °C | 74.97 °C |
| 18100 mSec | 113.22 °C | 45.04 °C | 6 | 37200 mSec | | 127.90 °C | 75.71 °C |
| 21700 mSec | 122.02 °C | 51.26 °C | 7 | 38200 mSec | | 125.42 °C | 78.73 °C |
| 25300 mSec | 129.86 °C | 57.89 °C | 8 | 39200 mSec | | 123.35 °C | 77.85 °C |
| 28900 mSec | 136.85 °C | 64.08 °C | 9 | 40200 mSec | | 121.56 °C | 79.56 °C |
| 0 mSec | 0.00 °C | 0.00 °C | 10 | 41200 mSec | | 119.83 °C | 80.47 °C |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |
| 0 mSec | 0.00 °C | 0.00 °C | | | | | |

FIG. 15

THERMOGRAPHIC ANALYSIS OF POLYMERIC MATERIALS

This application is the U.S. National Phase application under 35 U.S.C. § 371 of International Application No. PCT/GB2015/052307, filed Aug. 10, 2015, published as WO 2016/027064 on Feb. 25, 2016, which claims the benefit of GB Patent Application Number 1414666.6 filed Aug. 19, 2014. These applications are hereby incorporated by reference herein.

This invention relates to polymeric materials and parts made therefrom. Particularly, although not exclusively, the invention relates to a method of assessing a part which comprises a polymeric material and apparatus relating thereto. Preferred embodiments involve assessing a part in the form of a plaque thereby to obtain results indicative of how a preform, made from the same composition as the plaque, may perform upon heating during a stretch blow moulding process. Other embodiments may be used to assess how a sheet may perform in thermoforming applications, for example in thermoformed packaging applications.

Containers used to package many consumer products are made from polymeric materials, for example polyester, particularly poly(ethylene terephthalate) (PET). A process for producing such containers involves making a PET preform and reheat stretch blow molding the preform into a container, typically a bottle. Reheating involves passing the preforms between banks of heat lamps which heat the outside of the preforms and then heat passes through the preforms by conduction.

Preforms must have properties that permit them to function in the container manufacturing process and containers produced must be capable of maintaining the integrity of the product in the container for prolonged periods. The final properties of a stretch blow molded container are a strong function of the blow moulding temperature, including the temperature of both the inside and outside surfaces of the preform.

Compositions for making stretch blow moulded containers or thermoformed packaging may vary significantly. Such compositions include a polymeric material. However, the properties of such polymeric materials, for example when reheated, may vary as between different types and grades of materials. In addition, the compositions suitably include a reheat additive. This may be added to the composition to improve heat-up rates and allow the rate of blowing containers from preforms or thermoforming from sheets to be increased. In addition, reheat additives may be included to provide energy savings for polymer processing and/or to reduce cycle times. The compositions may include other additives, for example colourants, UV blockers, acetaldehyde scavengers and stabilisers.

It is very difficult to predict how different compositions having different levels and types of additives may function in a stretch blow moulding process or in thermoforming. For example, a composition which includes a black pigment may absorb heat rapidly and transmit it across a preform. However, this may lead to preferential crystallisation on the outside of the preform. If, on the other hand, the composition includes a white pigment, the pigment may reflect heat and, consequently, passage of heat to the inner surface of the preform may be restricted. It is also difficult to predict how preforms having different wall thicknesses may function in a stretch blow moulding process. Similar problems exist in thermoforming processes.

Apparatus and methods for assessing a polymeric part during heating have been proposed. For example, EP1342550A1 (Eastman) discloses a method and device for predicting temperature profiles throughout the thickness of a polymer preform used in a container reheat stretch blow moulding process, by measuring the outside surface temperature of a preform or a series of preforms at least two times during the period the preform is cooling down, after exiting a heat station, and before entering a blow moulding station in a blow moulding machine and calculating the temperature distribution throughout the thickness of the preform, based upon the measured outside surface temperatures, using a novel algorithm. However, the method is largely predictive, simply being based on a measurement of outside surface temperatures. It is believed that users of the apparatus and method can have little confidence in any results, particularly when new compositions are being assessed. In addition, users need access to expensive and large scale stretch blow moulding machines to apply the algorithm.

WO2009/109777 A1 (Queens University) discloses a method for providing an internal surface temperature profile of a thermoplastic preform during a stretch blow moulding production process comprising at least the steps of: (a) heating a plurality of in-line cold preforms in the production process to provide a plurality of in-line heated preforms; (b) diverting at least one of the in-line heated preforms to provide at least one off-line heated preform; (c) providing the remaining in-line heated preforms to one or more stretch blow moulds for forming the heated preforms into blow moulded products; and (d) locating one or more temperature sensors inside the or each off-line heated preform of step (b) to provide an inside surface temperature profile of said preform(s).

However, disadvantageously, the method involves assessing a preform taken from a line during reheat stretch blow moulding. Such a method is not suitable for rapidly assessing a wide range of compositions to assess their suitability and/or heating characteristics during reheating.

US2011/0236518 A1 (Sidel) also assesses actual preforms on a reheat stretch blow moulding line by use of temperature probes which are inserted into preforms during their passage along the line. Disadvantageously, any method which involves testing on a line is expensive, risks significantly wastage of materials if bottles produced from the preforms are defective and does not allow rapid collation of results for multiple different compositions which may be used to produce preforms.

Thus, the aforementioned prior art processes rely on use of an expensive large scale stretch blow moulding machine; provide no practical way of defining a temperature profile of a composition assessed through the entire blow moulding process; and produce large amounts of scrap materials.

It is an object of the invention to address problems associated with assessing polymeric parts, for example preforms, during heating.

According to a first aspect of the invention, there is provided apparatus for assessing a part which comprises a polymeric material, the apparatus comprising:
(i) a holder for holding a part to be assessed;
(ii) a radiation source for subjecting a part held in the holder to radiation to heat the part;
(iii) a first sensor for assessing the temperature of a first surface of a part held in the holder and a second sensor for assessing the temperature of a second surface of the part held in the holder;
(iv) a recording device which communicates with the first and second sensors for recording information relating to temperatures assessed by the temperature sensors.

Said radiation source is preferably arranged to emit infrared (IR) radiation for heating the part. It may comprise a halogen lamp. The lamp may be rated at less than 2000 W, for example less than 1000 W or less than 750 W or preferably less than 500 W. It may be operated at less than 15 A, for example at 13 A. Thus the lamp (and suitably the entire apparatus) may be operated using a domestic power supply, for example a single phase power supply.

The radiation source may be arranged on one side, suitably outside, for example above, the holder. It is suitably arranged to direct radiation towards an outer, for example, upper, surface of a part to be assessed when held in said holder. It is suitably arranged to direct radiation towards a plane, for example a main plane, of a part to be assessed.

Said apparatus preferably includes a window. Said holder is preferably arranged to be positioned on one side of the window (e.g. on an inside or lower side) and said radiation source is arranged to be positioned on an opposite side (e.g. on an outside or upper side). Said radiation source is preferably arranged to direct radiation through the window. The holder is suitably arranged to be positioned directly adjacent, for example, below, the window, whereby the radiation source is able to expose to radiation, via said window, a part held in said holder. Said radiation source is preferably arranged to expose less than 95% or less than 90% or less than 80% of the area of a first surface of said part, for example a surface (e.g. plane) of said part which is closest to the radiation source in use. Said radiation source is preferably arranged to expose at least 30% or at least 50% of the area of said first surface. The window preferably defines the area of a surface of the part to be assessed which is to be exposed to radiation from said radiation source in use. Said window preferably has an area (suitably via which radiation may pass) in the range 50 to 10000 mm$^2$, preferably 100 to 8000 mm$^2$, especially 500 to 5000 mm$^2$. Said window is preferably circular. It may have a diameter of 10 mm to 100 mm, preferably in the range 20 mm to 80 mm. Said window may be made of a material which is a good transmitter of IR radiation but a poor thermal conductor. The thermal conductivity may be less than 5 W/(m·K), for example less than 3 W/(m·K). Said window may comprise a glass, for example quartz glass. The material of the window may have a thickness of less than 5 mm, for example less than 3 mm.

Said apparatus may include an air extractor for withdrawing air from around the radiation source and suitably moving the air away from a part held in the holder in use. This is suitably intended to minimise conduction of heat from air which may be heated by the radiation source to a part held in use, in said holder. This aims to ensure (as far as possible) that any rise in temperature of a part held in said holder is due to absorption of IR radiation from said radiation source, rather than from conduction of heat from the lamp and/or surrounding areas. The air extractor is suitably also arranged to withdraw air from adjacent the holder (and therefore from around a part held in the holder in use). To this end, one or more air passages may be defined between the holder and the air extractor via which air can flow from a position adjacent the holder to the extractor. Said one or more air passages may be defined in a component which surrounds the window (when provided).

Said air extractor may include a motorized fan for withdrawing air as aforesaid. An outlet of the air extractor may be positioned at least 10 cm or at least 15 cm downstream of said radiation source and/or said window (when provided).

Said first sensor is preferably arranged to assess temperature without contacting a part held in said holder in use. Said first sensor is preferably arranged to measure surface emissivity. It is preferably an IR sensor. Said first sensor is preferably arranged to assess temperature in less than 100 ms.

Said second sensor is preferably arranged to assess temperature without contacting a part held in said holder in use. Said second sensor is preferably arranged to measure surface emissivity. It is preferably an IR sensor. It is preferably arranged to assess temperature at the same rate as said first sensor.

Said holder is preferably arranged so the first sensor can be positioned on a first side of the holder and the second sensor can be positioned on a second side of the holder. Thus, suitably, in use, a part held in the holder can be positioned so its first surface faces the first sensor and its second surface faces the second sensor and, suitably, the first and second sensors are on opposite sides of the part. Said first surface may be a first plane of the part and said second surface may be a second plane of the part wherein, suitably, said first and second planes are parallel. Said first and second surfaces are, suitably, two surfaces of the part which have the greatest surface areas. The surface area of the first and second surfaces may each be in the range 500 to 5000 mm$^3$, suitably 1000 to 4000 mm$^3$, preferably 1500 to 3500 mm$^3$.

Said first sensor may be arranged, in use, to be spaced a distance of 50 to 200 mm from the holder; and said second sensor may be spaced a distance of 50 to 200 mm from the holder. The distance between the first and second sensors may be at least 100 mm; and is preferably less than 400 mm. Said first and second sensors are preferably aligned. Suitably they are arranged to assess temperature, in use, at a first position on one side (e.g. the side of said first plane) of the part and at a second position on an opposite side (e.g. the side of said second plane) of the part and preferably said first and second positions are superimposed.

Said holder for the part is suitably arranged to minimise conduction of heat away from the part. This may involve minimising contact of the part with solid material.

The holder is preferably arranged to releasably secure the part to be assessed in position, suitably so the part is substantially immovably secured in position relative to the holder.

Said holder preferably includes a plurality of (e.g. at least 3, preferably only 3) elements which contact a surface (I) of the part in use. Said surface (I) may be annular. It may extend parallel to the first and second surfaces of the part. Said surface (I) preferably extends around said second surface of the part (which may be an inside or lower surface in use). Said surface (I) may have a width of 5 mm to 20 mm. The area of surface (I) contacted by said element may be less than 20 mm$^2$, for example less than 10 mm$^2$.

Said elements preferably comprise a thermal insulator. For example, they may comprise a material, having a thermal conductivity of less than 0.7 W/(m·K) for example less than 0.4 W/(m·K). Said elements may comprise a synthetic polymeric material, for example a fluorocarbon or polyaryletherketone or sulphone.

Said holder preferably includes a plurality of abutments which contact a surface (II), for example a perimetric surface, of the part in use. Said surface (II) may extend substantially perpendicular to surface (I). Said surface (II) preferably extends around said second surface of the part. Said surface (II) may have a width of 1.5 mm to 5 mm. The area of said surface (II) contacted by said abutments may be less than 20 mm$^2$, for example less than 10 mm$^2$.

Said abutments preferably comprise a thermal insulator. For example, they may comprise a material having a thermal conductivity of less than 0.7 W/(m·K) for example less than 0.4 W/(m·K). Said elements may comprise a synthetic polymeric material, for example a fluorocarbon or polyaryletherketone or sulphone.

Said holder preferably includes a resilient component for releasably securing the part in the holder. The resilient component may be arranged to contact said surface (II) of said part in use.

Said holder preferably includes a stepped region (e.g. an annular stepped region) and suitably the part is arranged in use to be seated within the stepped region.

In use, a part with a total surface area, defined as "x" $cm^2$, may be held in the holder and assessed. The total surface area of the part which is in contact with a solid body (when the part is held in the holder) may be defined as "y" $cm^2$. Suitably x/y is greater than 400. Thus, the majority of the part is not in contact, in use, with any solid body and, consequently, an air gap is defined around substantially the entire extent of the part which may therefore minimise conduction of heat away from the part and contribute to the reproducibility of results obtained using the apparatus.

The percentage of surface area of the part in use which is contacted by any solid body (e.g. said elements or said abutments) is preferably less than 5%, especially less than 1%.

Said holder is preferably movable between a first position and a second position. In said first position, the holder may be positioned adjacent the radiation source so a part held in the holder, in use, can be subjected to radiation to heat the part. In said second position, the holder may be positioned adjacent the first and second sensors, so the sensors can assess the temperature of the first surface and second surface of the part held in the holder, in use. Said first and second positions are suitably spaced apart so that, in use, the linear distance between the centre of a part held in the holder when in said first position and the centre of the part held in the holder in the second position is at least 10 cm and is less than 30 cm.

Said holder is preferably arranged to pivot to move between said first position and said second position. It may pivot through at least 30°, preferably at least 60°, more preferably at least 80°, between its first and second positions. It may pivot through less than 120° between its first and second positions.

Said holder may comprise a region for holding a part to be assessed and a pivot, suitably spaced from the region. For example, the centre of a part held in the holder and said pivot may be spaced apart by at least 10 cm.

Said holder may be movable to a third position, spaced from said first and second positions. Said third position may be arranged to allow access to the holder to enable a part to be assessed to be engaged with the holder. Said holder is preferably arranged to pivot from said first and/or second positions to said third position. It may be arranged to pivot through at least 30°, preferably at least 60° or at least 80°, from either said first position or said second position thereby to locate it in said third position.

Said holder may be movable to a fourth position, spaced from said first, second and third positions. The apparatus is suitably arranged for ejection of a part from said holder when in said fourth position.

Said recording device which communicates with the first and second temperature sensors is preferably a computer. Said recording device is preferably arranged to record information relating to temperatures assessed by the sensors and information relating to the time the temperatures were assessed. Said recording device is suitably arranged to record information relating to at least ten temperatures assessed by each of the first and second temperature sensors together with information relating to at least ten different times when information relating to the temperatures was assessed.

Said apparatus preferably includes a computer arranged to control movement of the holder between first and second positions as described. The computer may be arranged to control the time the holder is present in the first position.

Said apparatus preferably includes a computer arranged to control operation of said first and second sensors.

A single computer preferably acts as said recording device; controls movement of the holder between its first and second positions; and controls operation of said first and second sensors.

Said apparatus for assessing a part is preferably arranged, for example via a or said computer, for an operator to specify one or more of the following:
(i) the output level of the radiation source;
(ii) the number of measurements to be taken by said first and second temperature sensors;
(iii) the time a part to be assessed is exposed to said radiation source between measurements taken by said first and second temperature sensors.

Preferably, an operator may specify and/or select each of (i), (ii) and (iii).

Said apparatus is preferably arranged and/or programmable for the first temperature sensor to make temperature assessments of a part at a rate of at least 1 assessment (for example at least 2 assessments) per 10 seconds; and said second temperature sensor is preferably arranged to make temperature assessments at the same rate as said first sensor.

Said apparatus is preferably arranged for said first and second temperature sensors to assess temperatures at the same time.

The apparatus may be used in the method of the second aspect.

The invention extends to said apparatus in combination with a part to be assessed, for example a plaque, which is suitably held in said holder. The part may have any feature of the part described hereinafter.

According to a second aspect of the invention, there is provided a method of assessing a part which comprises a polymeric material, the method comprising:
(i) selecting a part to be assessed;
(ii) subjecting the part to radiation to heat the part;
(iii) assessing the temperature of a first surface of the part and recording information relating to the temperature assessed;
(iv) assessing the temperature of a second surface of the part and recording information relating to the temperature assessed;
(v) repeating step (iii) at a later time;
(vi) repeating step (iv) at a later time.

Said method is preferably for assessing the temperature profile of said first and second surfaces over time when exposed to said radiation. Said part may comprise a polymeric material and said method may be for assessing the effect different additives have on absorption of radiation by said part and/or how the temperatures of the first and second surfaces change over time. Said method may be for assessing the effect of reheat additives included in said part. Reheat additives are suitably IR absorbing materials. They may be carbon—black based or may be commercially available for example from Polytrade or Colormatrix under the trade marks React Heat and Smart Heat. Said method may be used to predict how a preform made from the same composition as said part may perform upon heating during a stretch blow moulding process; or to predict how a sheet made from the same composition as said part may perform in a thermoforming process.

Said part may comprise a polymeric material which is a thermoplastic. It may comprise any thermoformable polymeric material. Said polymeric material may be selected from polyesters (e.g. PET), polyolefins and polycarbonates.

Said part may include said polymeric material and an additive, for example a reheat additive. A reference to "ppm" herein refers to "parts per million by weight". Said part may include 1 to 1000 ppm, for example 1 to 500 ppm reheat additive. Said part may include at least 95 wt %, for example at least 99 wt % of said polymeric material.

The volume of material defining said part (i.e. the volume of the part excluding any void areas thereof) may be in the range 5000 $mm^3$ to 200,000 $mm^3$, preferably in the range 5000 $mm^3$ to 100,000 $mm^3$, more preferably in the range 7000 $mm^3$ to 80000 $mm^3$. Said part may have a maximum dimension which is less than 15 cm, preferably less than 10 cm. Said part may have a thickness of less than 10 mm; and preferably at least 2 mm. Said part may have a width (e.g. a diameter when the part is circular) in the range 20 to 100 mm, for example in the range 40 to 80 mm. Said part preferably has a circular cross-section. Said part is preferably a plaque.

Said first and second surfaces of the part may have any feature described according to the first aspect. Said first and second surfaces are preferably parallel. Said first and second surfaces preferably face in opposite directions.

The method preferably comprises releasably securing the part in a holder having any feature of the holder of the first aspect.

In step (ii), the method preferably comprises directing radiation towards only one surface (e.g. said first surface) of the part and suitably to no other surface of the part. The method preferably uses a radiation source having any feature of the radiation source of the first aspect. Thus, the method preferably comprises subjecting the part to IR radiation. The method may comprise subjecting the part to radiation for less than 120 seconds, especially for less than 60 seconds during the entire process—e.g. from step (i) to a step which comprises removal of the part from an apparatus in which the method is carried out.

The method may comprise assessing the temperature of said first and second surfaces by a method which does not involve contact with said first and second surfaces. Said method may comprise measuring the surface emissivity of said first and second surfaces. Said method may involve use of a first sensor and a second sensor having any feature described according to the first aspect.

In steps (iii) and (iv) information is suitably recorded by a computer. The computer may be arranged to display information relating to the temperatures of the first and second surfaces over time.

In the method a or said computer preferably controls the time when the temperatures of the first and second surfaces is assessed.

Step (iii) is preferably repeated at least 5 times, preferably at least 10 times.

Step (iv) is preferably repeated at least 5 times, preferably at least 10 times.

The method preferably comprises withdrawing air from around the radiation source, suitably during step (ii). This may be undertaken using an air extractor which may have any feature of the air extractor of the first aspect.

Step (ii) of the method is preferably undertaken with a part arranged in a first position.

Step (iii) is preferably undertaken with the part arranged in a second position, spaced from said first position. Said part may be secured in a holder as described and preferably the holder (including said part) is movable between said first and second positions. Said holder and/or its movement between said first and second position may be as described according to the first aspect.

In the method, the time taken to move from said first position to said second position may be less than 0.5 seconds, for example less than 0.2 seconds. The method preferably comprises moving the part from the first position to the second position and back to the first position in less than 1 second, preferably less than 0.5 seconds. In the method, steps (iii) and (iv) are preferably undertaken whilst the part is stationary in the second position in between movement of the part from the first position to the second position and back to the first position.

In the method, the part may be stationary in the second position for less than 0.5 seconds, for example less than 0.25 seconds during movement of the part from the first position to the second position and back to the first position.

The method preferably comprises repeating the sequence of movements of the part from the first position to the second position and back to the first position at least 8 times.

In steps (iii) and (iv), the temperature may be assessed in less than 100 milliseconds.

Preferably, said later time of step (v) is less than 5 seconds after step (iii). Step (iii) is preferably repeated at least 5 times in less than 30 seconds.

Preferably, said later time of step (vi) is less than 5 seconds after step (iv). Step (iv) is preferably repeated at least 5 times in less than 30 seconds.

Prior to step (ii), the method may comprise an operator selecting one or more of the following:
  (i) the output level of a radiation source used to heat the part;
  (ii) the number of times steps (iii) and (iv) are to be repeated;
  (iii) the time for which the part is subjected to radiation in step (ii) before the temperature is assessed in steps (iii) and (iv).

Prior to step (ii), the method may comprise connecting apparatus for carrying out the method to electrical power rated at no more than 250V and 13 Amps.

After step (vi), the method may comprise selecting a second part, suitably which is different from said part (e.g. in terms of additives incorporated into a polymeric material of said part or dimensions of the part) and assessing the second part by repeating step (i) to (vi) on said second part. Results obtained from assessing said first part and said second part may then be compared.

The method may comprise, additionally, undertaking steps (iii) and (iv) before step (ii)—e.g. after a conditioning step. Steps (iii) and (iv) may also be undertaken during cooling of the part after completion of subjecting the part to radiation Said method of said second aspect preferably uses apparatus according to the first aspect.

Specific embodiments of the invention will now be described, by way of example, with reference to the accompanying drawings, in which, FIG. 1 is a perspective view, from the front, of apparatus for assessing reheat characteristics of a polymeric plaque, with a quadrant of a support disc of the apparatus cut-away and with the plaque in an ejection position;

FIG. 15 is a sample Test Report detailing parameters used and results obtained in the testing of a plaque;

In the figures, the same of similar parts are annotated with the same reference numerals. Also, some figures include some parts omitted in the interests of clarity.

Figure 1:
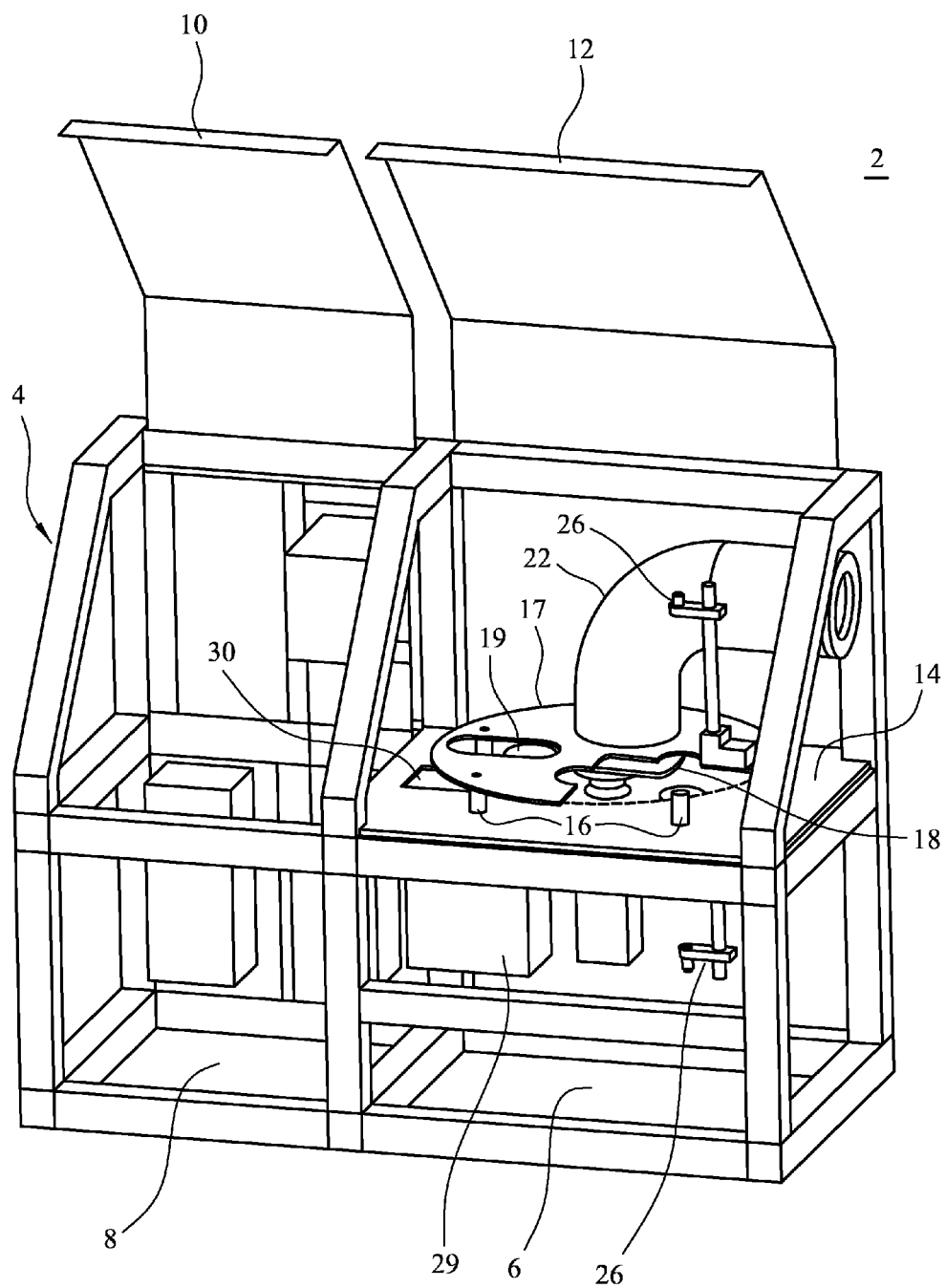
Figure 2:
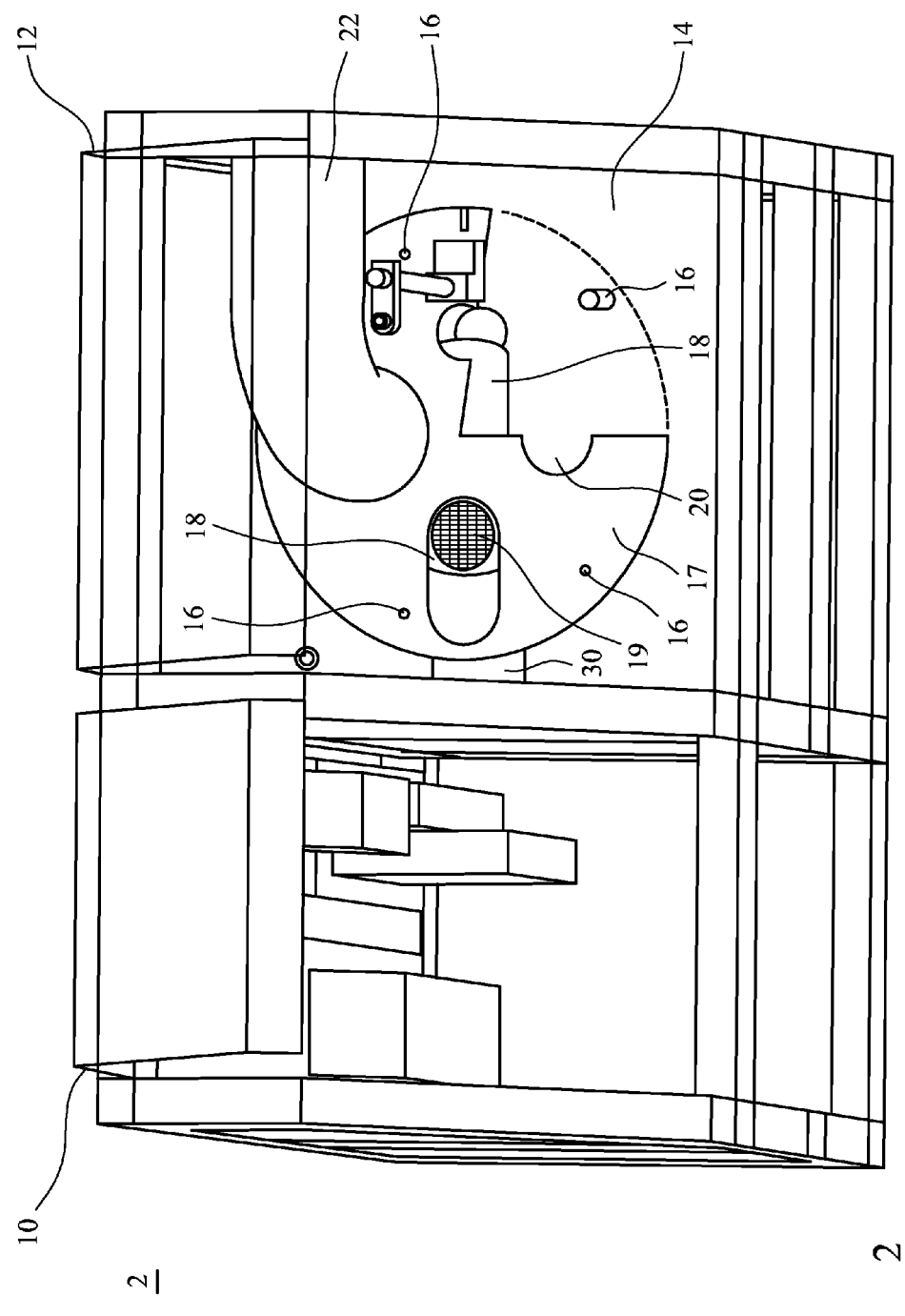
FIG. 2 is a perspective view from the top of the apparatus, with a quadrant of a support disc of the apparatus cut-away and with the plaque in an ejection position.

Apparatus 2, shown in FIGS. 1 and 2, includes a housing 4 divided generally into a measurement part 6 and a processing and control part 8, wherein parts 6, 8 are fitted with pivotable lids 10,12. Although not represented in FIGS. 1 and 2, the housing includes solid walls which define a fully enclosed structure. The apparatus is positioned in a temperature-controlled environment, for example an air-conditioned room. The temperature of the room is suitably set at 23° C. Alternatively and/or additionally, the temperature within housing 4 could be thermostatically controlled.

Within the measurement part 6 is a platform 14 on which is supported, via spaced apart posts 16, a stationary rigid support disc 17. Between the platform 14 and disc 17, plaque holder 18 is rotatably mounted. The plaque holder is arranged to hold a plaque 19 and move the plaque between four positions relative to the disc 17. In an input position, the plaque holder 18 is arranged directly underneath opening 20 (FIG. 3) which is arranged so a plaque can pass through the opening for engagement with the plaque holder.

In a measurement position, which is 90° from the input position, there are provided first and second temperature measuring assemblies 24, 26 arranged to measure the temperature of the top and bottom surfaces of a plaque held in the plaque holder.

Figure 3:
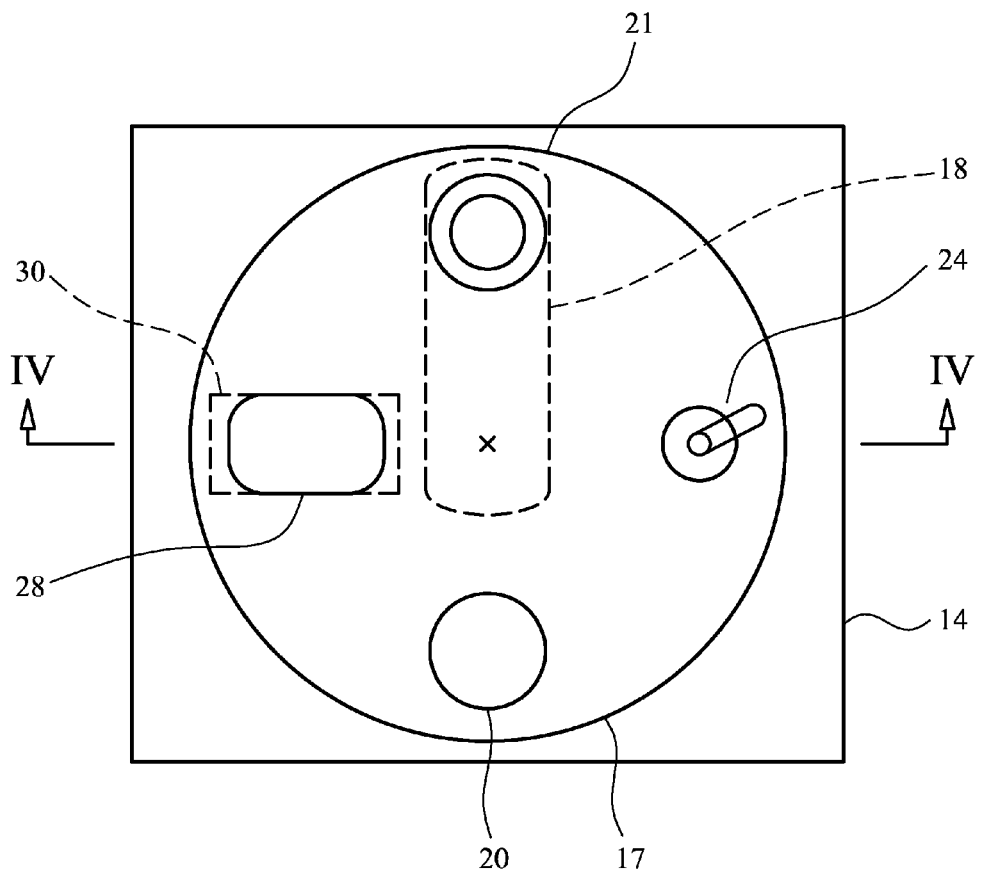
FIG. 3 is a schematic plan view of part of the apparatus, with the plaque in a heating position.

The plaque holder can be rotated through 90° from the measurement position to a heating position (referenced 21 in FIG. 3), wherein the plaque is positioned directly below a heat lamp (not shown in FIG. 3) contained within a housing 22 (shown in FIGS. 1 and 2 but not FIG. 3).

In an ejection position, diametrically opposite the measurement position, the disc 17 includes an oval shaped opening 28 arranged to allow the plaque to be ejected from the plaque holder by urging the plaque upwardly before it is directed into a container 29 via a rectangular opening 30 in platform 14.

Prior to introduction into the apparatus a plaque to be assessed is conditioned by heating it to 23° C. in an incubator.

Then, with the plaque holder 18 in the input position, the conditioned plaque to be assessed is engaged with the holder and the holder rotated to the measurement position, wherein the temperatures of the top and bottom surfaces of the plaque are measured and recorded. Then, the plaque holder is rotated through 90° to the heating position, wherein the plaque is heated by the lamp for a predetermined time which is programmed into the apparatus and is between 0.01 seconds to 999.99 seconds. Then the plaque holder is rapidly rotated back to the measurement position, wherein the temperatures of the upper and lower surfaces of the plaque are again rapidly measured. The holder is then rotated back to the heating position and heating continued for a predetermined time before the plaque holder is again rotated to the measurement position wherein again the temperatures of the upper and lower surfaces of the plaque are measured. The time taken for the holder to move from, and back to, the second position is 0.35 seconds. When in the measurement position, the temperature measuring assemblies 24, 26 take four readings, each taking 30 milliseconds and the average of the four readings is used in subsequent analysis. Thus, the total time the plaque is in the measurement position is 0.12 seconds. This sequence of heating and temperature assessment is repeated many times (e.g. so that the plaque is subjected to ten or more temperature measurements over a time of 30 to 60 seconds (although this time could be lengthened or shortened). The temperature measurements and the time of the measurements are relayed to a computer within control part 8. The computer provides an output to a user on how the upper and lower surfaces of the plaque heat up over time.

Further details on the apparatus and its functioning are described below.

Figure 5:
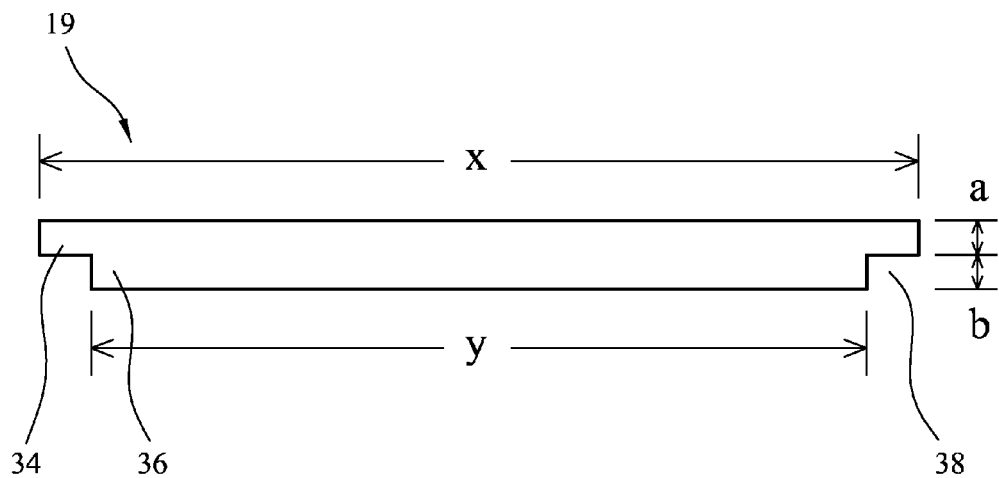
FIG. 5 is a cross-section through a first plaque.

A plaque 19 for assessment in the apparatus is shown in FIG. 5. The plaque is made by injection moulding from a composition comprising a polymeric material and a specific amount of reheat additive(s) and any other additives(s) to be assessed. Alternatively, the plaque may be formed by being pressed from a 2.5 mm sheet. The plaque has a first body part 34, of circular cross-section, having a diameter "x", of 60 mm and a thickness "a", of 2.5 mm; and a second body part 36, of circular cross-section, having a diameter, "y", of 50 mm and a thickness, "b", of 2.5 mm. (In other embodiments, thickness "b" may be selected within the range 2.5 to 10 mm). A stepped region 38 is defined between the first and second body parts 34, 36. Although the plaque is described as comprising first and second body parts, it should be appreciated that the parts comprise a single injection moulded (or pressed) component which is homogenous and/or monolithic.

The plaque is arranged to be engaged in opening 32 in the plaque holder so the plaque is restrained and is therefore substantially immovable during rotation of the plaque holder. In addition, contact between the plaque holder and the plaque is minimized and an air gap is defined between the two. By minimizing contact, conduction of heat away from the plaque to the plaque holder is minimized. If significant heat is conducted from plaque to the plaque holder in use, it has been found that the temperatures of the upper and lower surfaces of the plaque are affected and results collated using the apparatus are less representative of how, for example, a preform made to the same composition/thickness would perform.

Figure 7:
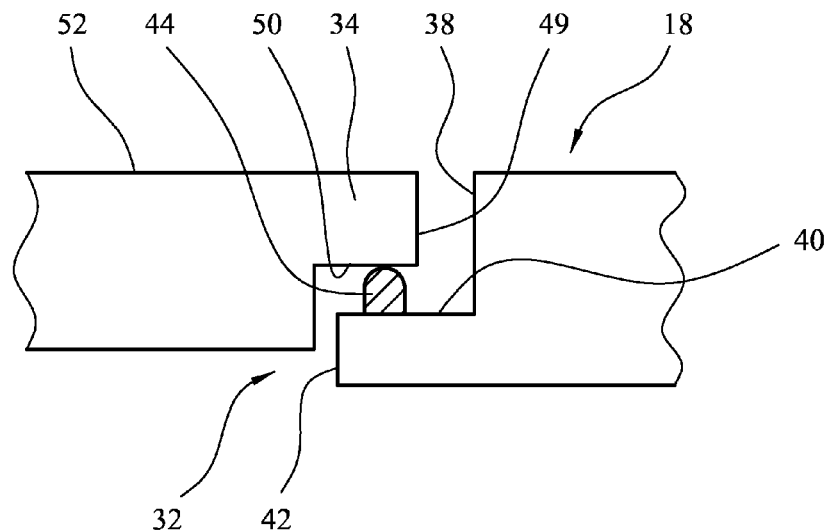
FIG. 7 is a cross-section along line VII-VII of FIG. 6 with the plaque engaged in an opening in the plaque holder.
Figure 6:
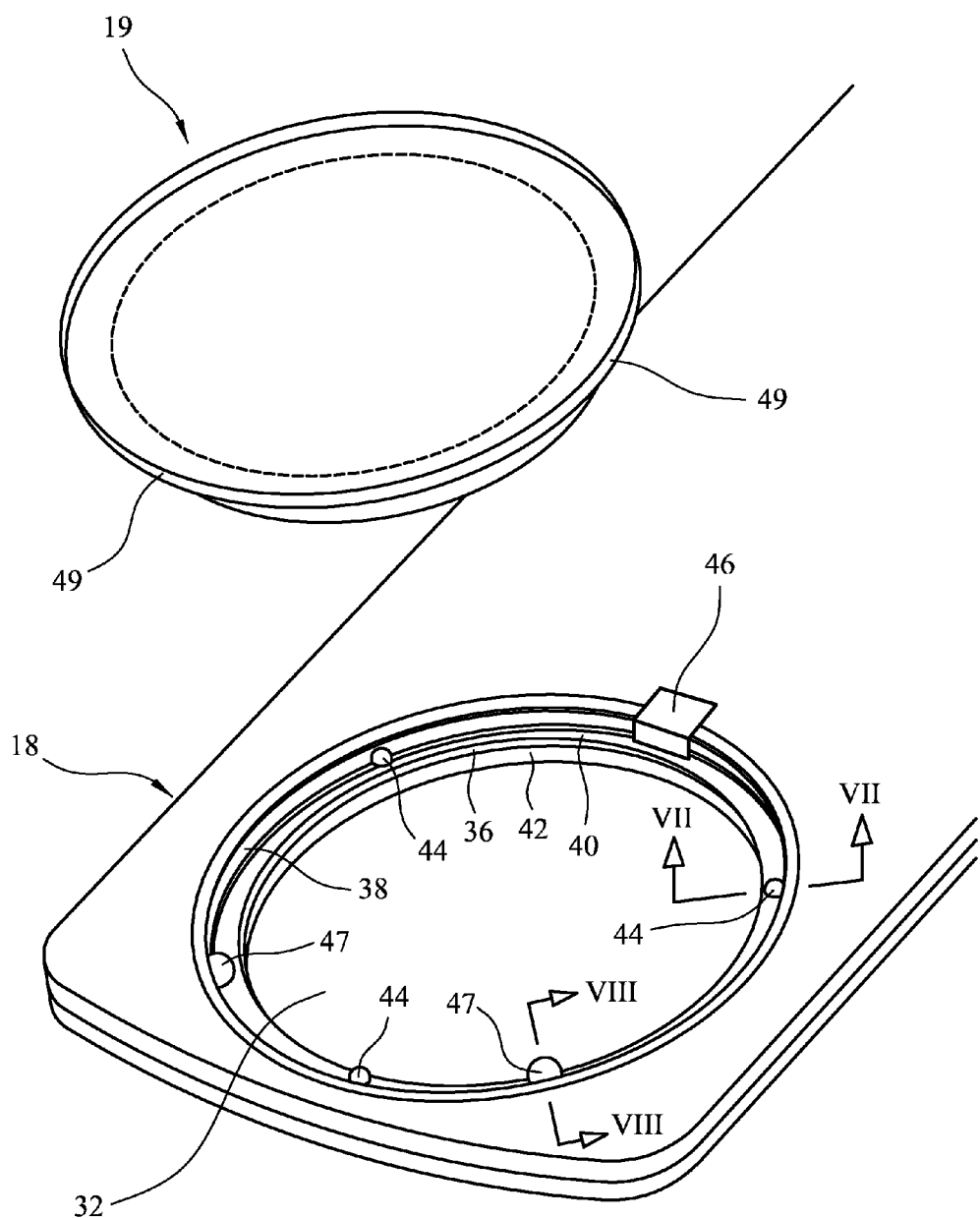
FIG. 6 is a perspective view from the top of a plaque prior to engagement with a plaque holder.

Referring to FIGS. 6 and 7, opening 32 of the plaque holder 18 is defined by a circumferential stepped region 36 which includes a first vertical circumferential wall 38, a horizontal circumferential wall 40 and a second vertical circumferential wall 42. Three support dowels 44, which are circumferentially spaced apart by 120°, extend upwardly from wall 40. The dowels 44 have a dome-shaped head and are made from a thermally insulating material, for example from a fluorocarbon resin or polyetheretherketone (PEEK). Two abutments 47 (FIGS. 6 and 8), spaced 120° apart, extend inwardly from wall 38. The abutments have dome-shaped heads which are arranged to contract circumferential end face 49 of plaque 19. A narrow spring clip 46 is arranged to resiliently contact end face 49 of the plaque to urge the plaque against abutments 47. The abutments 47 and clip 46 are made from a thermally insulating material as for dowels 44.

Figure 8:
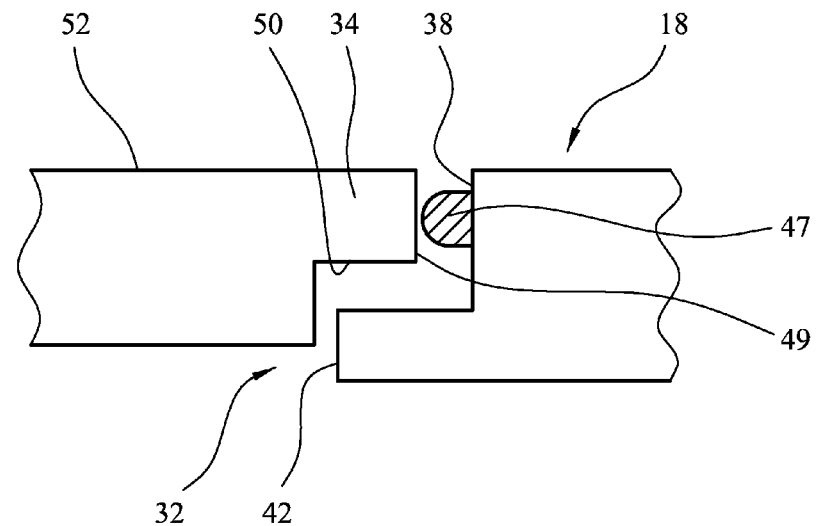
FIG. 8 is a cross-section along line VIII-VIII of FIG. 6.

As represented in FIGS. 7 and 8, the plaque is secured within the plaque holder with lower surface 50 of first body part 34 abutting and being supported on the three dowels 44. The clip 46 resiliently engages end face 49 and urges the plaque against abutments 47 so the plaque is substantially immovably fixed in position. The plaque is only contacted by the three dowels 44 on its lower surface 50, two abutments 47 on its perimeter and by clip 46. Other than the aforementioned, an air gap is defined around the plaque. Thus, conduction of heat away from the plaque in use is minimized.

Figure 9:
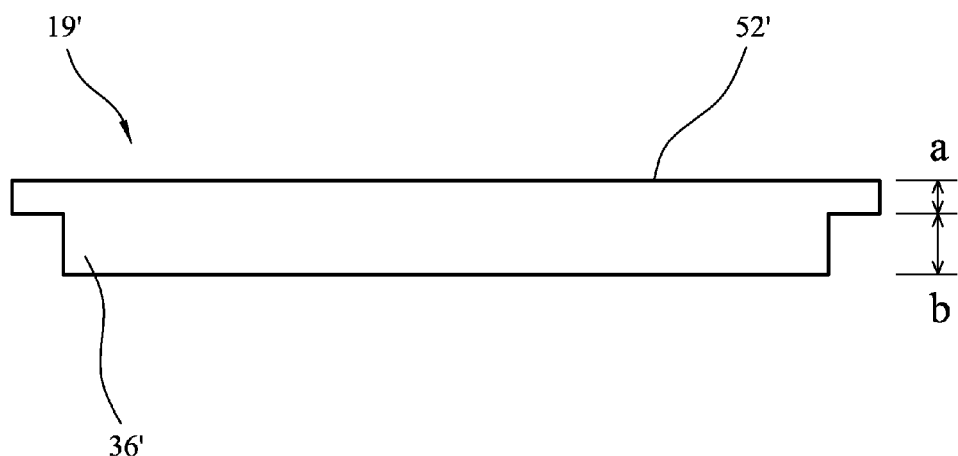
FIG. 9 is a cross-section through a second plaque.
Figure 10:
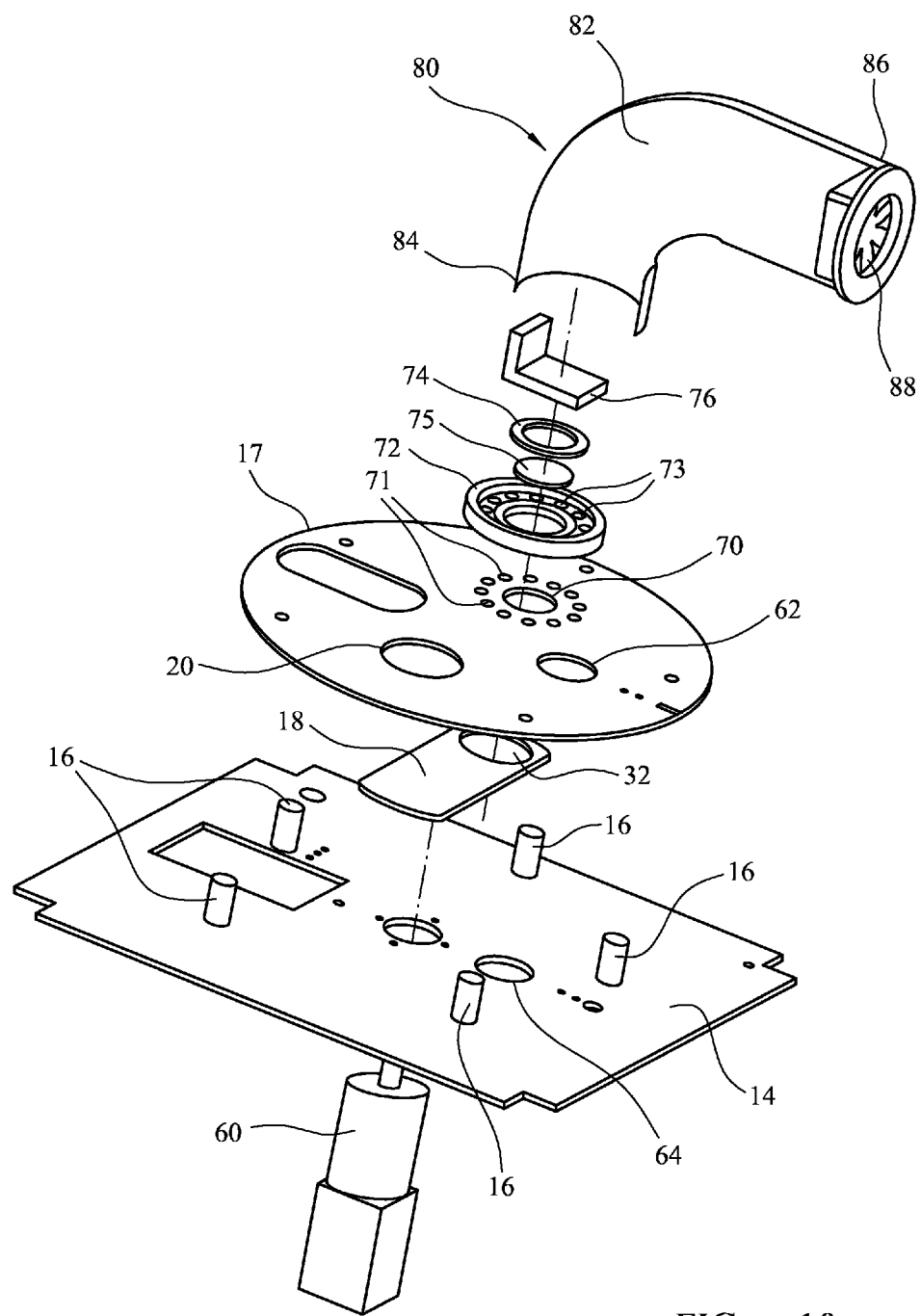
FIG. 10 is an exploded view of part of the apparatus.
Figure 11:
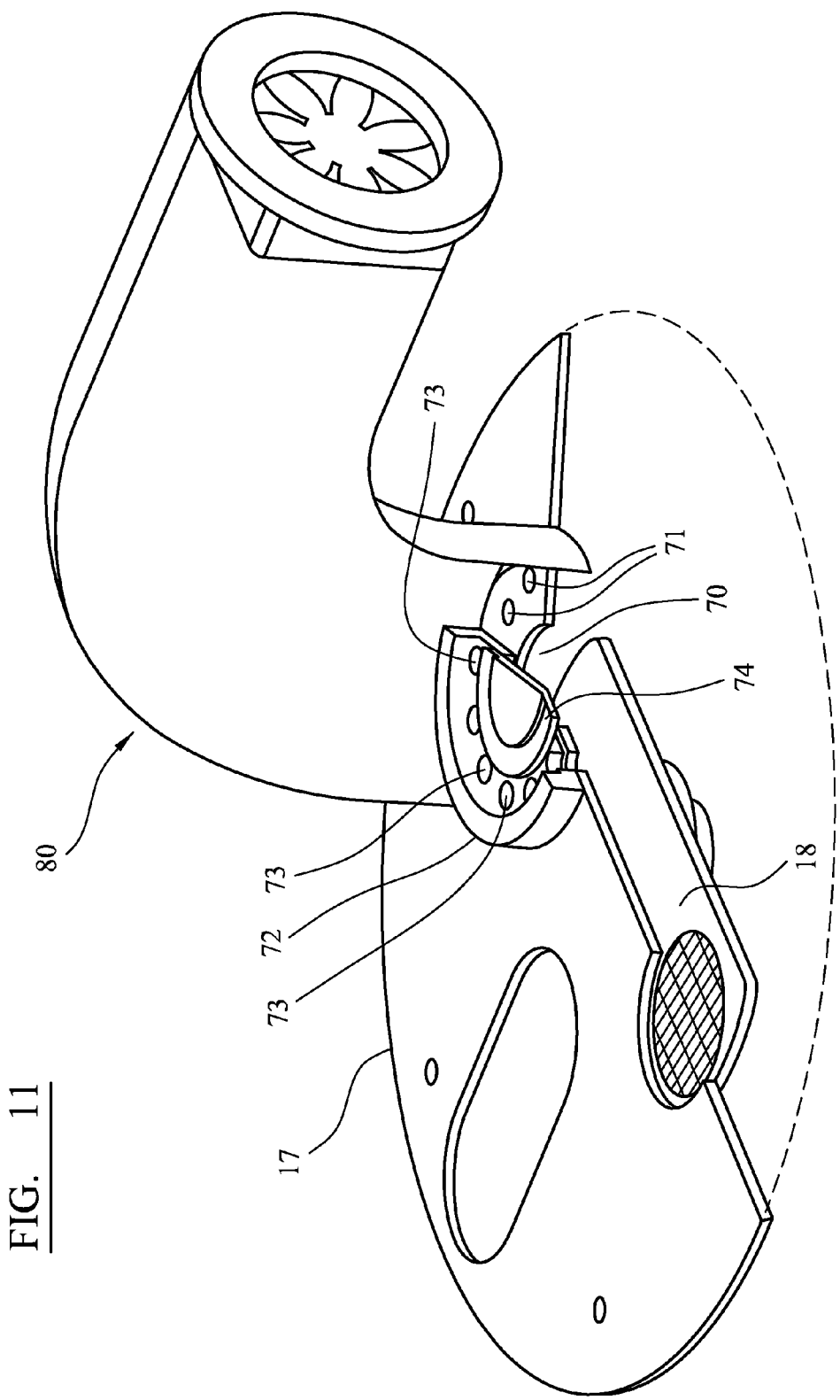
FIG. 11 is a view of part of the apparatus with the plaque in an input position and with a support disc (and other parts) of the apparatus cut-away.
Figure 12:
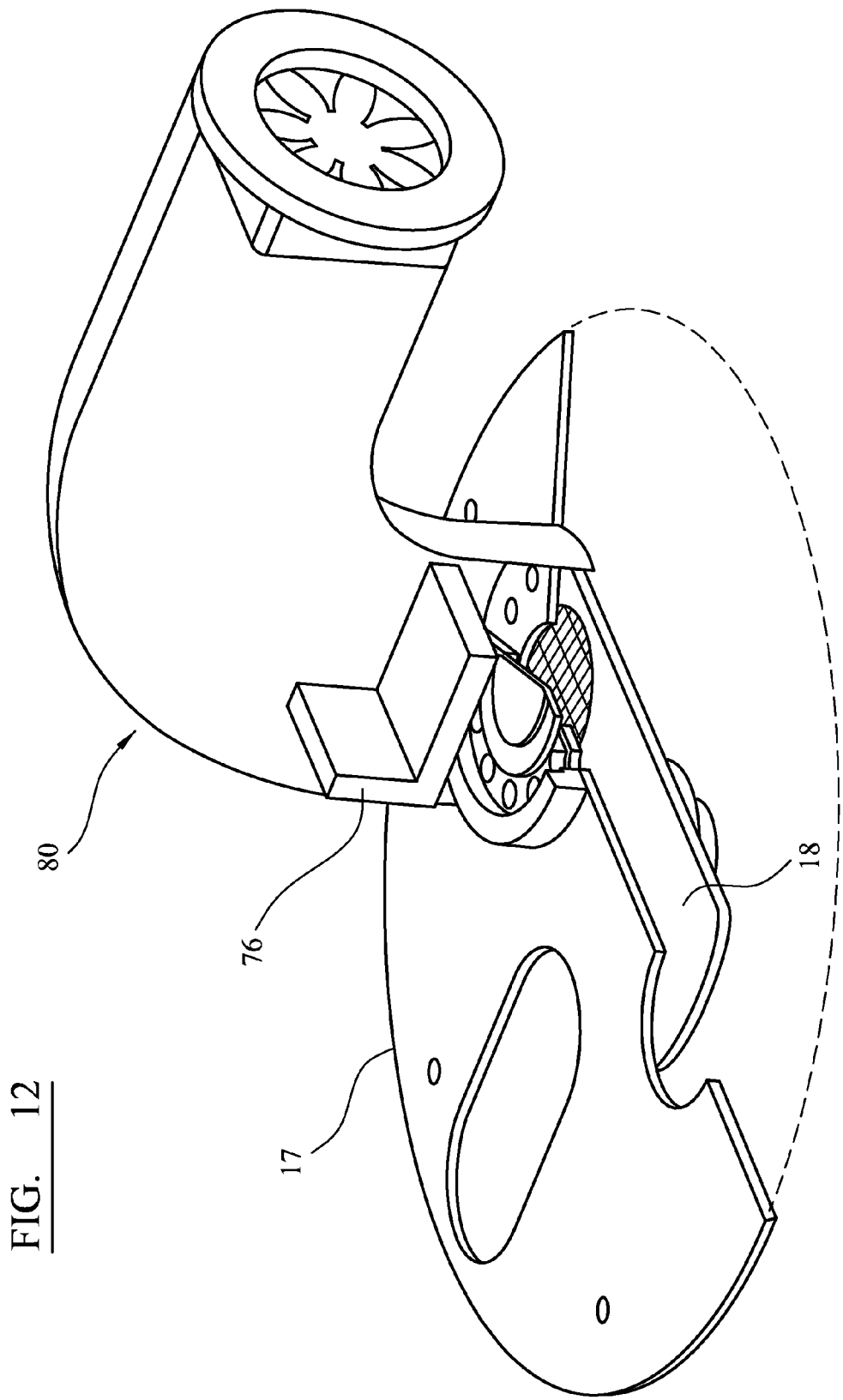
FIG. 12 is a view similar to FIG. 10, except with the plaque in a heating position and a lamp for heating shown.
Figure 13:
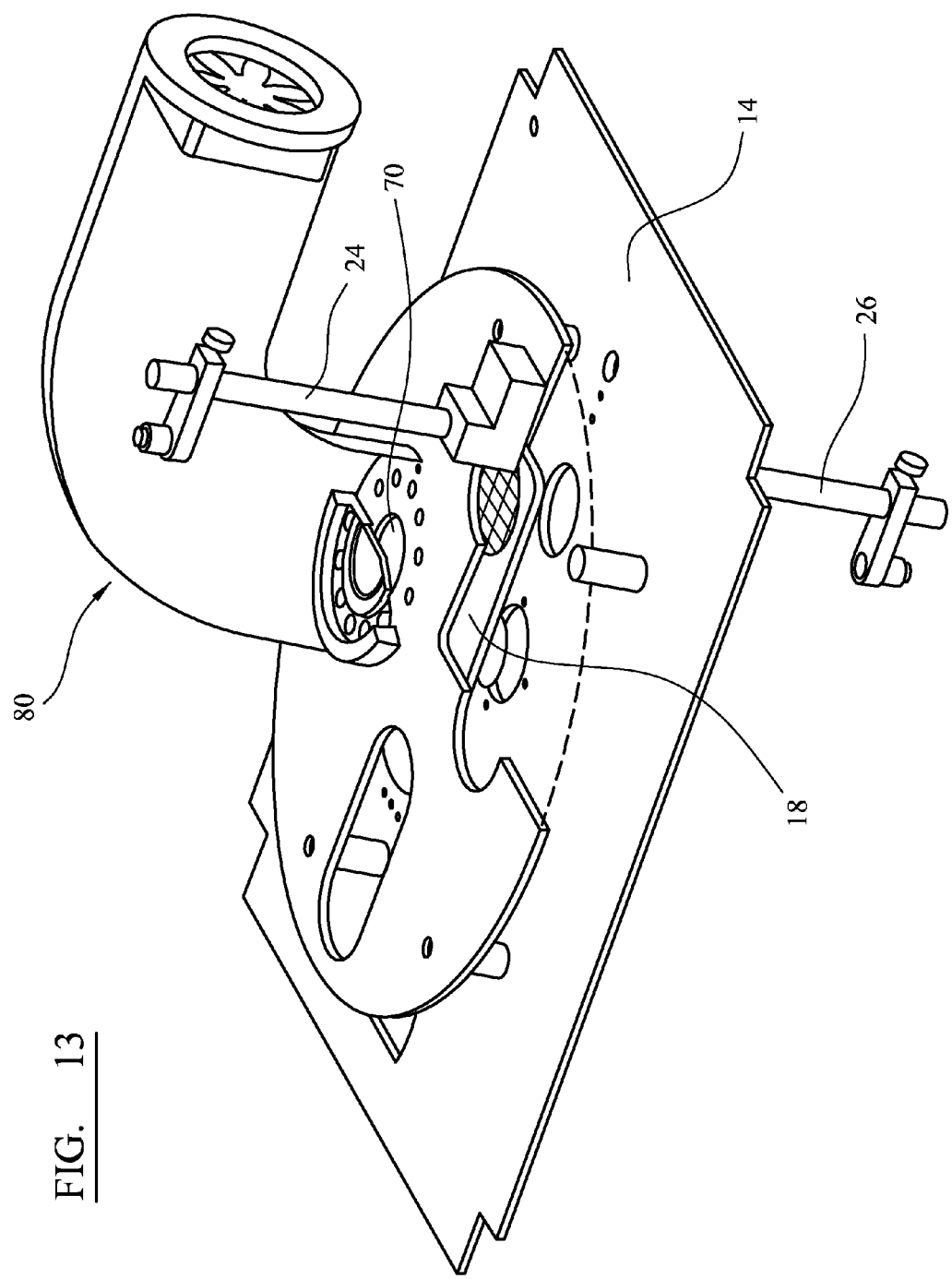
FIG. 13 is a view similar to FIGS. 11 and 12, except with the plaque in a measurement position and with temperature measuring assemblies and a platform shown.
Figure 14:
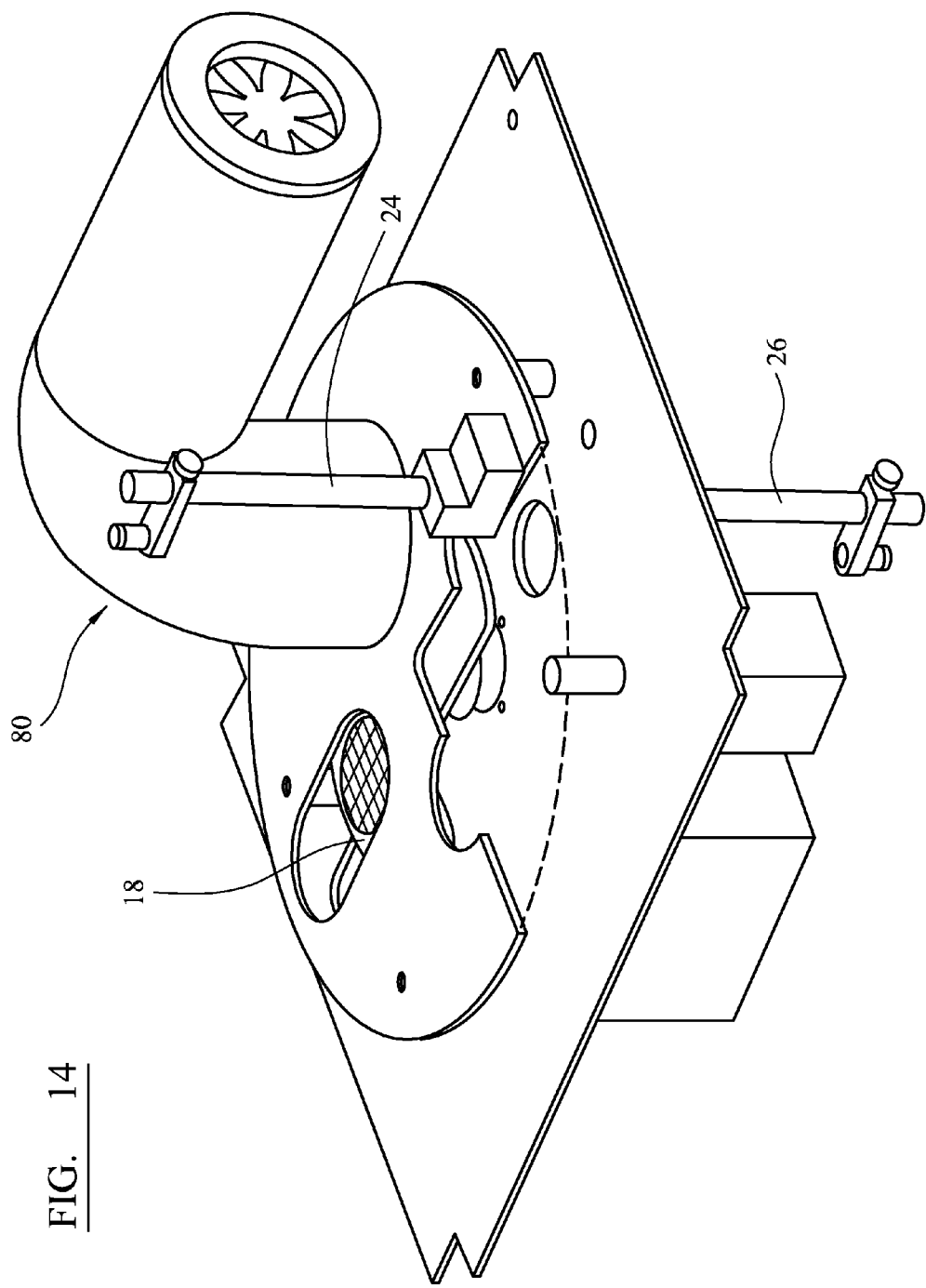
FIG. 14 is a view similar to FIG. 13, except with the plaque in an ejection position and with an extraction unit shown as fully enclosed.

It is desirable to be able to assess plaques of different thicknesses thereby to simulate container preforms of different thicknesses. Thus, the plaque holder may releasably engage a plaque 19', shown in FIG. 9, having a thickness "a" of 2.5 mm and a thickness "b" of 7.5 mm. The plaque can be engaged with the plaque holder 18 as described for the plaque of FIG. 5 with upper surface 52' of the plaque being positioned and/or aligned with the holder as shown for plaque 52 in FIG. 8; but with the second body part 36' of the plaque extending downwardly more than plaque 19 due to the extra thickness of plaque 19'. Plaques of other sizes may be produced. In each case, however, the upper surfaces 52, 52' of the plaques are in the same position when engaged with the plaque holder. This ensures the distance between the plaque and the lamp for heating the plaque is constant, thereby allowing ready comparison between results obtained with plaques of different thicknesses.

The polymeric material in the composition of the plaque may be any polymeric material which may be used in a process wherein it is desirable to assess how the composition heats up over time. It is suitably a polyester (e.g. PET) or it could be polypropylene.

Additional features of the apparatus are shown in more detail in FIGS. 10 to 14.

The apparatus includes an electric motor 60, under the control of a computer via an encoder which is arranged to rotate the plaque holder 18 between its four positions.

The support disc 17 (see FIG. 10) includes a circular cross-section opening 62 which is axially aligned with a circular cross-section opening 64 in the platform 14 and openings 62,64 are arranged to be axially aligned with opening 32 in the plaque holder 18 when the plaque holder is in its measurement position.

Figure 4:
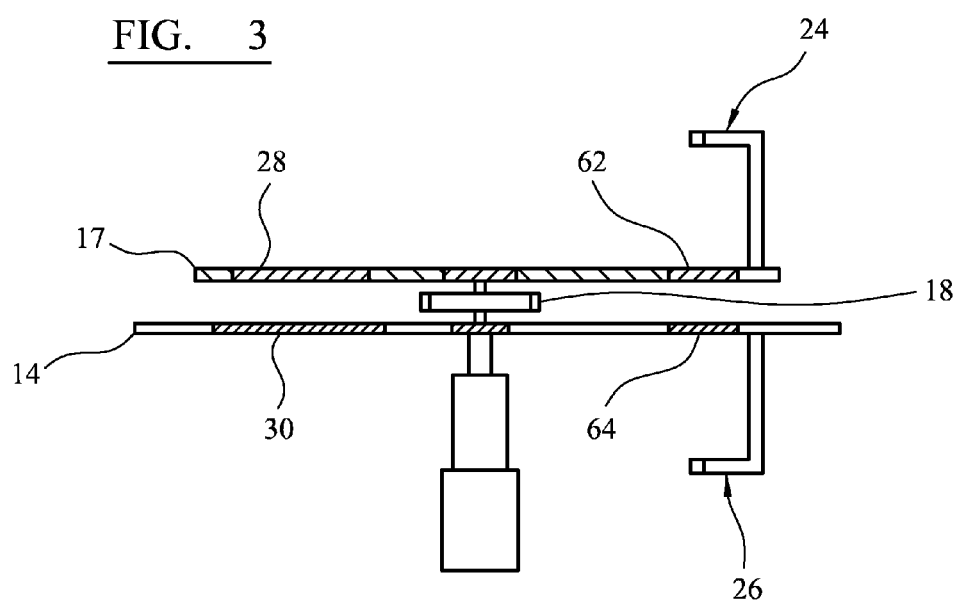
FIG. 4 is a cross-section along line IV-IV of FIG. 3.

First and second temperature measuring assemblies 24, 26 (see FIGS. 4, 13 and 14) include respective IR sensors which are axially aligned with openings 62, 64 and are arranged to measure the surface emissivity of the respective upper and lower surfaces of the plaque when the plaque holder and associated plaque are in the measurement position. The surface emissivity is converted to temperature by software associated with the apparatus 2. The IR sensors provide a non-contact method of assessing surface emissivity, For example, the sensors may measure emissivity to a penetration depth of approximately 10 μm maximum. The sensors are controlled by the computer and communicate information, including emissivity information, to the computer.

The support disc 17 includes an opening 70 (FIGS. 10 and 11) in the heating position which is axially aligned with the plaque holder 18 when the plaque holder is in the third position. Around opening 70 are smaller openings 71. A collar 72 is secured to the disc 17 so that openings 73 in the collar are superimposed upon openings 71. A quartz glass window 75 and a sealing gasket 74 engage the collar. The collar 72 and gasket 74 are made from a material with low thermal conductivity, for example a fluoropolymer, PEEK or ceramic. Furthermore, the quartz glass window 75 is a good transmitter of IR radiation but a poor transmitter of heat. Thus, the arrangement of the components in the heating position is optimised to allow transmission of IR radiation but to minimise transmission of heat to a plaque held in the plaque holder.

The quartz window has a diameter of 50 mm and its area defines the area of the plaque on which IR radiation is incident when the plaque is in the heating position. Thus, IR radiation is only incident on a central region of a proportion (e.g. a 50 mm diameter area) of the upper surface of the plaque having a diameter of 60 mm, By not irradiating a 5 mm wide band adjacent the perimeter of the plaque, the amount of white light emitted from the edge of the plaque is limited, thereby limiting the amount of IR radiation which may escape (and not heat) the plaque. This helps to optimize the validity of results obtained using the apparatus.

Above the quartz glass window 75 is a lamp 76 which is arranged to emit IR radiation in the direction of the plaque when it is in the heating position. Suitably, the lamp is rated at 500 W and operates at 13 A which means the apparatus can be operated using a domestic power supply. The lamp may be a tungsten halogen lamp. IR radiation emitted by the lamp is primarily captured by any IR absorbing reheat additive incorporated in the composition of the plaque. In view of the design of, and materials used for, components of the apparatus, minimal thermal energy (heat) is transmitted from the lamp to the plaque. This substantially ensures that any rise in temperature of the plaque is due to absorption of IR radiation rather than conduction of heat. Accordingly, results collated are representative of how the composition and/or thickness of the plaque affect reheat. Such results can be extrapolated to predict how a preform having the composition and/or thickness may perform in a reheat stretch blow moulding process.

An extraction unit 80 is fixed to the support disc 17 at the heating position. The unit 80 is arranged to extract air from in and around the heating position so as to minimise the conduction of thermal energy from the air to the plaque. Unit 80 includes a conduit 82 which is sealed at its lower end 84 to disc 17. Downstream of end 84 the conduit curves and defines a horizontal section which terminates at end 86 with a motorised extraction fan 88. The fan 88 is arranged to draw air through aligned openings 71, 73 to remove thermal energy from around the plaque. The speed of fan 88 can be controlled so it is representative of ventilation in a relevant stretch blow moulding machine.

After assessment of a plaque, the plaque holder can be rotated to the ejection position (FIG. 14) wherein the plaque is ejected from plaque holder into the container 29 (FIG. 1). The plaque holder may then be returned to the input position ready for receiving a further plaque to be assessed.

Further features of the apparatus in use will now be described.

A plaque 19 for assessment is made as described above. Then data relevant to proposed testing of the plaque is input into the computer of the apparatus 2. Such data is summarized in a Test Report, part of which is as shown in FIG. 15. Note: other results (not shown) may be summarized in a similar manner. Examples of variables/data included in the Tet Report are as follows:

Test Name—user defined test identifier.
Polymer ID—polymer used to make plaque.
Additive ID—additive incorporated in the plaque
Additive Rate—refers to the Let-Down-Ratio (LDR)
Additive Concentration—self-explanatory
Lamp Power—the power of heat lamp 76. This may be adjusted.
Number of samples—this refers to the number of times the plaque is moved to the second position and the temperatures of its top and bottom surfaces assessed.
Individual Heat Exposure Time—This refers to the time the plaque is exposed to the heat lamp between each temperature measurement of the plaque.
Starting Air Temp—self-explanatory (reported to confirm apparatus (excluding plaque) is in a steady state).
Starting Steel Work Temp—self-explanatory (reported to confirm apparatus (excluding plaque) is in a steady state).
Ending Air Temp—self-explanatory (reported to confirm apparatus (excluding plaque) is in a steady state).
Ending Steel Work Temp—self-explanatory (reported to confirm apparatus (excluding plaque) is in a steady state).

The test report of FIG. 15 also includes some results. The "heating steps/samples" shows how the top and bottom surfaces of the plaques heat up over time when exposed to the lamp. Referring to FIG. 15, the initial top and bottom plaque temperatures (at 100 mSec) are assessed and, thereafter, the temperature is assessed every 3600 mSec. Note that the time the plaque is under measuring assemblies 24, 26 when in the second position is only 31 mSec. During this time, in view of the very fast response time of assemblies 24, 26, four temperature measurements of respective top and bottom surfaces of the plaque are taken. These are then averaged and reported as shown in FIG. 15. The "conditioning step/samples" show how the temperature of at top and bottom surfaces varies over time after the lamp has been turned off.

Figure 16:
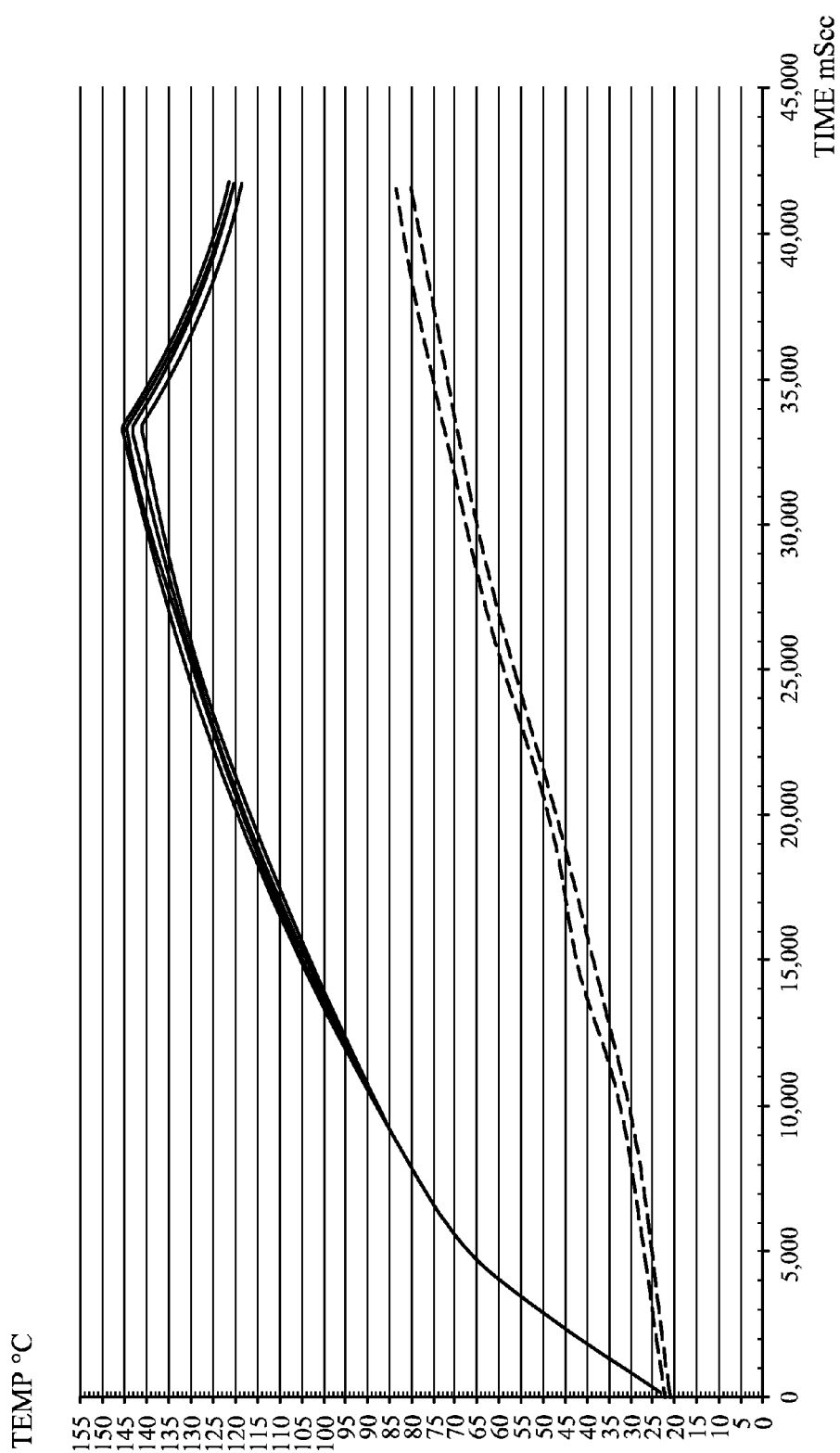
FIG. 16 is a graph of temperature (° C.) v. time (mSec) for the top and bottom surfaces of identical test samples.

To illustrate how results obtained may be represented, reference is made to FIG. 16. The upper line includes results of assessments of the top surfaces of multiple identical plaques under identical conditions. The lower line includes results for the bottom surfaces of the plaques. It should be noted that the results for the identical plaques are superimposed thereby confirming the apparatus produces reproducible results.

Figure 17:
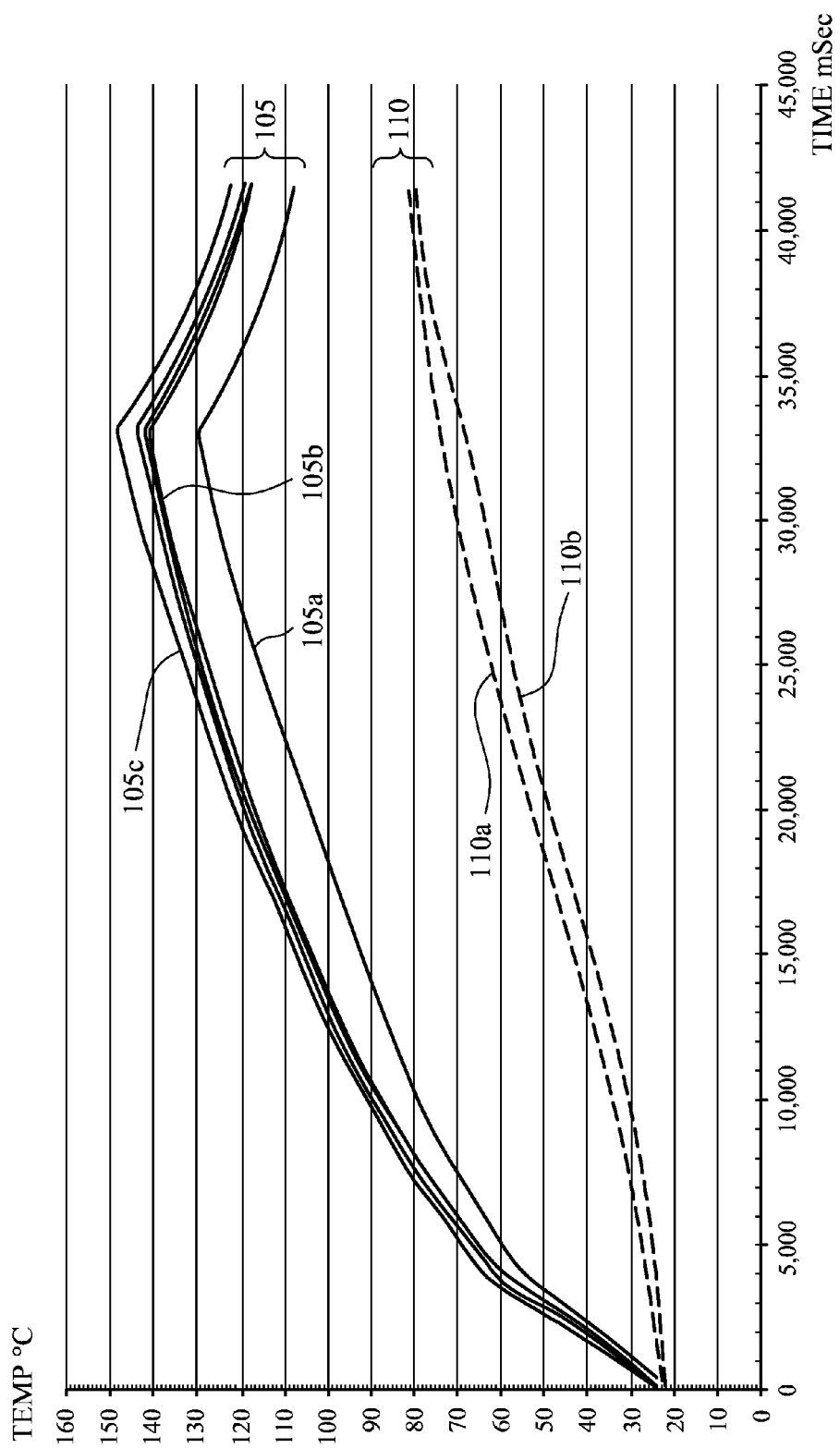
FIG. 17 is a graph of temperature (° C.) v. time (mSec) for the top and bottom surfaces of different test samples.

To illustrate other types of results which may be obtained, reference is made to FIG. 17. The figure includes lines 105, 110 which illustrate results for measurements of respective top and bottom surfaces of plaques. Lines 105a and 110a relate to the same plaque. In this case it will be noted that the temperature differences between upper and lower surfaces of the plaque are reduced compared to the other plaques. Although not illustrated, lines 105b include superimposed lines for top surfaces of several samples. For example, it includes a result for a Sample A which includes a white pigment but no titanium nitride (a known reheat additive). The bottom surface of Sample A is represented by line 110b. When a Sample B is tested (which is comparable to Sample A but includes titanium nitride), the result for the bottom surface is as for line 110b, but the top surface of Sample B is as for line 105c. This illustrates that adding titanium nitride causes the top surface to heat up more quickly, whilst having little effect on the bottom surface.

Thus, it should be appreciated that the apparatus described can have wide-ranging applications to assess the effect different reheat (and other) additives, incorporated at different levels, have on plaques (and therefore preforms). Assessments may be undertaken using different lamp powers and over a range of heat-up times. The results can be extrapolated to "real-life" situations to give useful information on how a range of reheat additives may perform against each other and/or how adjusting variables in stretch blow moulding may affect performance.

The apparatus may be used in a similar manner to assess plaques made of materials used in thermoforming applications, to facilitate selection of additives and other characteristics relevant to such applications.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. An apparatus for assessing a part which comprises a polymeric material, the apparatus comprising:
    (i) a holder for holding a part to be assessed;
    (ii) a radiation source for subjecting a part held in the holder to radiation to heat the part;
    (iii) a first sensor for assessing the temperature of a first surface of a part held in the holder and a second sensor for assessing the temperature of a second surface of the part held in the holder;
    (iv) a recording device which communicates with the first and second sensors for recording information relating to temperatures assessed by the temperature sensors;
    (v) wherein said holder is movable between a first position and a second position, wherein, in said first position, the holder is positioned adjacent to the radiation source so a part held in the holder, in use, can be subjected to radiation to heat the part; and in said second position, the holder is positioned adjacent to the first and second sensors, so the sensors can assess the temperature of the first surface and second surface of the part held in the holder, in use; and
    (vi) wherein the part is arranged, in use, to be moved from the first position to the second position and back to the first position.

2. The apparatus according to claim 1, wherein said radiation source is a lamp rated at less than 500 W.

3. The apparatus according to claim 1, wherein said radiation source is arranged to direct radiation towards an outer surface of a part to be assessed when held in said holder.

4. The apparatus according to claim 1, said apparatus including a window, wherein said holder is arranged to be positioned on one side of the window and said radiation source is arranged to be positioned on an opposite side, wherein said radiation source is arranged to direct radiation through the window.

5. The apparatus according to claim 1, wherein said radiation source is arranged to expose at least 30% of the area of the first surface of a part held in the holder.

6. The apparatus according to claim 1, wherein said radiation source is arranged to expose less than 95% of the area of the first surface of a part held in the holder.

7. The apparatus according to claim 1, said apparatus including an air extractor for withdrawing air from around the radiation source and moving the air away from a part held in the holder in use.

8. The apparatus according to claim 1, wherein said holder is arranged so the first sensor can be positioned on a first side of the holder and the second sensor can be positioned on a second side of the holder.

9. The apparatus according to claim 1, wherein said first and second sensors are aligned and are arranged to assess temperature in use, at a first position on one side of a part and at a second position on an opposite side of the part.

10. The apparatus according to claim 1, wherein said holder is arranged to pivot between said first position and said second position.

11. The apparatus according to claim 1, wherein said recording device is arranged to record information relating to temperatures assessed by the sensors and information relating to the time the temperatures were assessed.

12. The apparatus according to claim 1, wherein a single computer acts as said recording device, controls movement of the holder between its first and second positions and controls operation of said first and second sensors.

13. The apparatus according to claim 1, wherein said apparatus for assessing a part is arranged for an operator to specify one or more of the following:
   (i) the output level of the radiation source;
   (ii) the number of measurements to be taken by said first and second temperature sensors;
   (iii) the time a part to be assessed is exposed to said radiation source between measurements taken by said first and second temperature sensors.

14. The apparatus according to claim 1, wherein said apparatus is arranged and/or programmable for the first temperature sensor to make temperature assessments of a part at a rate of at least one assessment per 10 seconds; and said second temperature sensor is arranged to make temperature assessments at the same rate as said first sensor.

15. A method of assessing a part which comprises a polymeric material, the method comprising:
   (i) selecting a part to be assessed;
   (ii) subjecting the part to radiation to heat the part;
   (iii) assessing the temperature of a first surface of the part using a first sensor and recording information relating to the temperature assessed;
   (iv) assessing the temperature of a second surface of the part using a second sensor and recording information relating to the temperature assessed;
   (v) repeating step (iii) at a later time;
   (vi) repeating step (iv) at a later time;
   (vii) wherein step (ii) is undertaken with the part arranged in a first position; step (iii) is undertaken with the part arranged in a second position, spaced from said first position; and the method comprises moving the part from the first position to the second position and back to the first position.

16. The method according to claim 15, wherein said part comprises a polymeric material and said method is for assessing the effect different additives have on absorption of radiation by said part.

17. The method according to claim 15, wherein, in step (ii), the method comprises directing radiation towards only one surface of the part and to no other surface of the part.

18. The method according to claim 15, wherein step (iii) is repeated at least 5 times; and/or step (iv) is repeated at least 5 times.

19. The method according to claim 15, wherein the time taken to move from said first position to said second position is less than 0.5 seconds, wherein the method comprises repeating the sequence of movements of the part from the first position to the second position and back to the first position at least 8 times, and wherein step (iii) is repeated at least 5 times in less than 30 seconds; and step (iv) is repeated at least 5 times in less than 30 seconds.

20. An apparatus for assessing a part which comprises a polymeric material, the apparatus comprising:
   (i) a holder for holding a part to be assessed;
   (ii) a radiation source for subjecting a part held in the holder to radiation to heat the part;
   (iii) a first sensor for assessing the temperature of a first surface of a part held in the holder and a second sensor for assessing the temperature of a second surface of the part held in the holder;
   (iv) a recording device which communicates with the first and second sensors for recording information relating to temperatures assessed by the temperature sensors;
   (v) wherein said holder is movable between a first position and a second position, wherein, in said first position, the holder is positioned adjacent to the radiation source so a part held in the holder, in use, can be subjected to radiation to heat the part; and in said second position, the holder is positioned adjacent to the first and second sensors, so the sensors can assess the temperature of the first surface and second surface of the part held in the holder, in use;
   (vi) wherein the part is arranged, in use, to be moved from the first position to the second position and back to the first position;
   (vii) wherein said radiation source is a lamp rated at less than 500 W;
   (viii) wherein said radiation source is arranged to direct radiation towards an outer surface of a part to be assessed when held in said holder;
   (ix) wherein said apparatus including a window, wherein said holder is arranged to be positioned on one side of the window and said radiation source is arranged to be positioned on an opposite side, wherein said radiation source is arranged to direct radiation through the window;
   (x) wherein said apparatus including an air extractor for withdrawing air from around the radiation source and moving the air away from a part held in the holder in use;
   (xi) wherein said holder is arranged so the first sensor can be positioned on a first side of the holder and the second sensor can be positioned on a second side of the holder;
   (xii) wherein said first and second sensors are aligned and are arranged to assess temperature in use, at a first position on one side of a part and at a second position on an opposite side of the part;
   (xiii) wherein said holder is arranged to pivot between said first position and said second position; and
   (xiv) wherein said apparatus is arranged and/or programmable for the first temperature sensor to make temperature assessments of a part at a rate of at least one assessment per 10 seconds; and said second temperature sensor is arranged to make temperature assessments at the same rate as said first sensor.

* * * * *